US010328263B1

(12) United States Patent
Danilov et al.

(10) Patent No.: US 10,328,263 B1
(45) Date of Patent: *Jun. 25, 2019

(54) NON-INVASIVE NEUROMODULATION (NINM) FOR REHABILITATION OF BRAIN FUNCTION

(71) Applicants: Yuri P. Danilov, Middleton, WI (US); Mitchell E. Tyler, Madison, WI (US); Kurt A. Kaczmarek, Madison, WI (US)

(72) Inventors: Yuri P. Danilov, Middleton, WI (US); Mitchell E. Tyler, Madison, WI (US); Kurt A. Kaczmarek, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/602,060

(22) Filed: May 22, 2017

Related U.S. Application Data

(63) Continuation of application No. 14/615,766, filed on Feb. 6, 2015, now Pat. No. 9,656,078, which is a (Continued)

(51) Int. Cl.
*A61N 1/36* (2006.01)
*G09B 19/00* (2006.01)
*A61N 1/05* (2006.01)

(52) U.S. Cl.
CPC ....... *A61N 1/36103* (2013.01); *A61N 1/0548* (2013.01); *G09B 19/00* (2013.01);
(Continued)

(58) Field of Classification Search
CPC .................................................. A61N 1/36103
See application file for complete search history.

(56) References Cited

U.S. PATENT DOCUMENTS 2,055,540 A 9/1936 Karnofsky
3,851,651 A 12/1974 Icenbice
(Continued)

FOREIGN PATENT DOCUMENTS

EP 2671612 A1 12/2013
KR 20110038314 A 4/2011
(Continued)

OTHER PUBLICATIONS

Hamilton, "Impact of Acoustic and Tactile Multi-Modal Stimulation on Objective and Subjective Measures of Permanent Intractable Tinnitus: A Prospective Research Study," Hamilton Institute, National University of Ireland Maynooth, Jun. 2014.

*Primary Examiner* — Alyssa M Alter
(74) *Attorney, Agent, or Firm* — Proskauer Rose LLP

(57) ABSTRACT

In a patient suffering from neural impairment, stimulation is provided to sensory surfaces of the face and/or neck, or more generally to areas of the body that stimulate the trigeminal nerve, while performing an activity intended to stimulate a brain function to be rehabilitated. The simulation may then be continued after the performance of the activity has ceased. It has been found that the patient's performance of the activity is then improved after stimulation has ceased. Moreover, it tends to improve to a greater extent, and/or for a longer time, when the post-activity stimulation is applied, as compared to when post activity stimulation is not applied.

55 Claims, 10 Drawing Sheets

Related U.S. Application Data continuation of application No. 14/341,141, filed on Jul. 25, 2014, now Pat. No. 9,020,612, which is a continuation of application No. 14/340,144, filed on Jul. 24, 2014, now Pat. No. 8,909,345, which is a continuation of application No. 12/348,301, filed on Jan. 4, 2009, now Pat. No. 8,849,407.

(60) Provisional application No. 61/020,265, filed on Jan. 10, 2008, provisional application No. 61/019,061, filed on Jan. 4, 2008.

(52) U.S. Cl.
CPC .......... *A61N 1/361* (2013.01); *A61N 1/36067* (2013.01); *A61N 1/36078* (2013.01); *A61N 1/36092* (2013.01); *A61N 1/36096* (2013.01)

(56) References Cited

U.S. PATENT DOCUMENTS

| | | | |
|---|---|---|---|
| 4,865,048 A | 9/1989 | Eckerson | |
| 4,924,880 A | 5/1990 | O'Neill et al. | |
| 4,995,404 A | 2/1991 | Nemir | |
| 5,259,762 A | 11/1993 | Farrell | |
| 5,265,624 A | 11/1993 | Bowman | |
| 5,269,303 A | 12/1993 | Wernicke et al. | |
| 5,299,569 A | 4/1994 | Wernicke et al. | |
| 5,540,734 A * | 7/1996 | Zabara ............... | A61N 1/36082 600/26 |
| 5,553,626 A | 9/1996 | Burger et al. | |
| 5,792,067 A | 8/1998 | Karell | |
| 5,794,621 A | 8/1998 | Hogan et al. | |
| 5,878,154 A | 3/1999 | Schimmelpfennig | |
| 6,066,163 A | 5/2000 | John | |
| 6,089,864 A | 7/2000 | Buckner et al. | |
| 6,161,044 A | 12/2000 | Silverstone | |
| 6,169,781 B1 | 1/2001 | Doebert et al. | |
| 6,267,733 B1 | 7/2001 | Peterson et al. | |
| 6,326,901 B1 | 12/2001 | Gonzales | |
| 6,339,725 B1 | 1/2002 | Naritoku et al. | |
| 6,366,813 B1 | 4/2002 | DiLorenzo | |
| 6,366,814 B1 | 4/2002 | Boveja et al. | |
| 6,405,079 B1 | 6/2002 | Ansarinia | |
| 6,430,450 B1 | 8/2002 | Bach-y-Rita et al. | |
| 6,463,328 B1 | 10/2002 | John | |
| 6,526,318 B1 | 2/2003 | Ansarinia | |
| 6,546,291 B2 | 4/2003 | Merfeld et al. | |
| 6,556,868 B2 | 4/2003 | Naritoku et al. | |
| 6,954,668 B1 | 10/2005 | Cuozzo | |
| 7,228,178 B2 | 6/2007 | Carroll et al. | |
| 7,236,830 B2 | 6/2007 | Gliner | |
| 7,333,020 B2 | 2/2008 | Cohen et al. | |
| 7,483,747 B2 | 1/2009 | Gliner et al. | |
| 7,563,929 B2 | 7/2009 | Hobbs et al. | |
| 7,565,200 B2 | 7/2009 | Wyler et al. | |
| 7,640,062 B2 | 12/2009 | Shalev | |
| 7,672,730 B2 | 3/2010 | Firlik et al. | |
| 7,725,192 B2 | 5/2010 | Eskandar et al. | |
| 7,747,325 B2 | 6/2010 | DiLorenzo | |
| 7,768,499 B2 | 8/2010 | Sturtz | |
| 8,290,582 B2 | 10/2012 | Lin et al. | |
| 9,020,612 B1 | 4/2015 | Danilov et al. | |
| 9,656,069 B1 * | 5/2017 | Danilov .............. | A61N 1/36014 |
| 2003/0220677 A1 | 11/2003 | Doan et al. | |
| 2004/0073270 A1 | 4/2004 | Firlik et al. | |
| 2004/0073271 A1 * | 4/2004 | Harry .................. | A61N 1/0452 607/48 |
| 2005/0089829 A1 | 4/2005 | Wasowicz | |
| 2005/0197529 A1 | 9/2005 | Hoshihara et al. | |
| 2005/0203582 A1 | 9/2005 | Healy et al. | |
| 2005/0240253 A1 | 10/2005 | Tyler et al. | |
| 2006/0161218 A1 | 7/2006 | Danilov | |
| 2006/0241718 A1 | 10/2006 | Tyler et al. | |
| 2007/0248238 A1 | 10/2007 | Abreu | |
| 2007/0250119 A1 | 10/2007 | Tyler et al. | |
| 2007/0293917 A1 | 12/2007 | Thompson et al. | |
| 2007/0293918 A1 | 12/2007 | Thompson et al. | |
| 2008/0009772 A1 | 1/2008 | Tyler et al. | |
| 2008/0027510 A1 | 1/2008 | McClure et al. | |
| 2008/0082131 A1 | 4/2008 | Llanos | |
| 2008/0208287 A1 | 8/2008 | Palermo et al. | |
| 2008/0222670 A1 | 9/2008 | Lee et al. | |
| 2008/0228239 A1 | 9/2008 | Tyler et al. | |
| 2008/0233541 A1 | 9/2008 | De Vreese et al. | |
| 2008/0234604 A1 | 9/2008 | Burgmans | |
| 2008/0281550 A1 | 11/2008 | Hogle et al. | |
| 2009/0048647 A1 | 2/2009 | Tingey | |
| 2009/0082831 A1 | 3/2009 | Paul et al. | |
| 2009/0082839 A1 | 3/2009 | Lindquist et al. | |
| 2009/0312808 A1 | 12/2009 | Tyler et al. | |
| 2009/0312817 A1 | 12/2009 | Hogle et al. | |
| 2009/0326604 A1 | 12/2009 | Tyler et al. | |

FOREIGN PATENT DOCUMENTS

| | | |
|---|---|---|
| RU | 2215558 C2 | 11/2003 |
| RU | 2248227 C1 | 3/2005 |
| SU | 1068128 A | 1/1984 |
| WO | 02066111 A1 | 8/2002 |

\* cited by examiner

NON-INVASIVE NEUROMODULATION (NINM) FOR REHABILITATION OF BRAIN FUNCTION

CROSS-REFERENCE TO RELATED APPLICATIONS

This application is a continuation of, claims priority to and the benefit of, and incorporates by reference herein in its entirety, U.S. patent application Ser. No. 14/615,766, filed Feb. 6, 2015, now U.S. Pat. No. 9,656,078, which is a continuation of U.S. patent application Ser. No. 14/341,141, filed Jul. 25, 2014, now U.S. Pat. No. 9,020,612, which is a continuation of U.S. patent application Ser. No. 14/340,144, filed Jul. 24, 2014, now U.S. Pat. No. 8,909,345, which is a continuation of U.S. patent application Ser. No. 12/348,301, filed Jan. 4, 2009, now U.S. Pat. No. 8,849,407, which claims the benefit of and priority to U.S. Provisional Application No. 61/019,061 filed Jan. 4, 2008 and U.S. Provisional Application 61/020,265 filed Jan. 10, 2008, the entireties of which are incorporated by reference herein.

STATEMENT OF GOVERNMENT INTEREST

This invention was made with government support under grant NS048903 awarded by the National Institutes of Health. The Government has certain rights in the invention.

FIELD OF THE INVENTION

This document concerns an invention relating generally to treatment of neurological impairments, and more specifically to methods and devices for enhancing neurorehabilitation.

BACKGROUND OF THE INVENTION

Neurorehabilitation is an emerging field in medical science wherein patients suffering from damage to, or impairment of, all or a portion of their central nervous system (CNS) are treated to rehabilitate neural pathways, and/or establish new neural pathways, to at least partially compensate for the damage/impairment. Neurorehabilitation is therefore somewhat different from neural substitution, where devices are used to try to provide new neural inputs which serve as a proxies for impaired neural inputs—for example, devices which collect images of a patient's surroundings and then provide tactile feedback to the patient in dependence on the collected images, such that the patient is given tactile input as a substitute for visual input. Examples of neural substitution devices are described in prior patent applications which name the inventors of the present invention, e.g., US Published Patent Applns. 20050240253, US20060161218, 20060241718, 20070250119, 20080009772, and 20080228239 (all of which are incorporated by reference herein).

At the time this document was prepared, neurorehabilitation was commonly effected by non-invasive methods such as physical therapy, occupational therapy, or speech therapy, which basically involves the use of exercise to attempt to increase a patient's abilities. For example, one suffering from a spinal cord injury might exercise an affected area of the body to increase coordination and range of motion. These methods suffer from the disadvantage of being time-consuming, difficult and exhausting for the patient. Invasive methods also exist, such as electrostimulation, wherein electrodes are implanted to deliver electricity at or near neural pathways to enhance neural function, and/or to counter "erroneous" neural function. For example, deep brain stimulation (DBS) may be used for treatment of Parkinson's Disease and depression, left vagal nerve stimulation (LVNS) may be used for treatment of epilepsy, or sub-dural implantable stimulators may be used to assist with stroke recovery. These invasive methods are risky, still largely experimental, and expensive, and thus are generally used as a last resort when all other therapeutic interventions have failed. Additionally, they have not yet proven to be generally usable with other severe CNS disorders such as traumatic brain injury, stroke, or a sensory-motor polytrauma experienced by wounded military personnel, for example. It would therefore be useful to have additional methods and devices available for neurorehabilitation which are noninvasive or minimally invasive, inexpensive, and which eliminate or reduce the need for the ordeal of physical therapy and similar noninvasive methods.

SUMMARY OF THE INVENTION

The invention, which is defined by the claims set forth at the end of this document, is directed to methods—generally referred to herein as "non-invasive neuromodulation" or NINM—and NINM devices which at least partially alleviate the aforementioned problems. A basic understanding of some of the features of preferred versions of the invention can be attained from a review of the following brief summary of the invention, with more details being provided elsewhere in this document.

It has been found that neurorehabilitation can be assisted in a patient by having the patient engage in a task wherein the patient's ability to perform the task is hindered by impairment of the user's nervous system, and at the same time stimulating the patient's head and/or neck (or more specifically, providing stimulation detectable by one or more branches of the trigeminal nerve). For example, stimulation might be provided to the patient's face, tongue, forehead, ears, scalp, or neck while the patient attempts to maintain a normal posture, in the event of a patient with vestibular dysfunction (i.e., having difficulties with balance owing to impairment of the vestibular system); or while the patient moves his/her limb(s), in the case of apraxia (i.e., impairment of the ability to make purposeful/planned movement); or while the patient undergoes speech exercises, in the case of dysarthria (i.e., impaired speaking). It has been found that such stimulation can expedite neurorehabilitation, with the patient's ability to successfully perform the task being enhanced for at least some period of time after the stimulation ceases. Thus, for example, it has been found that where patients with vestibular dysfunction are subjected to stimulation while practicing posture/gait exercises, and they then cease the exercises and stimulation, their vestibular function is improved for at least a period of time thereafter, and for a longer period of time than if the stimulation was not provided. Thus, the foregoing methodology can be used to enhance the efficacy of conventional therapy.

The stimulation is preferably provided to the patient cutaneously (i.e., upon the patient's skin) so that it is noninvasive, though subcutaneous stimulation is also possible. The stimulation is preferably delivered by the use of stimulators, e.g., electrical elements (e.g., electrodes) for delivery of electrical stimulation, mechanical/electromechanical actuators (preferably piezo actuators, shape metal alloy actuators, MEMS actuators, or other compact devices), thermal elements (e.g., resistance heating elements or Peltier/Seebeck/Thomson elements), and/or electromagnetic elements (i.e., elements for emitting electromagnetic energy in the visible or invisible spectrum, e.g., radio wave emitters, microwave emitters, infrared emitters, ultraviolet emitters, etc.). In all cases, stimulation is delivered at intensities such that it is detectable by the patient's nerves, but at the same time such that tissue damage is avoided. Electrodes have been found to work well in practice, and are particularly preferred types of stimulators. These stimulators might be arrayed across all or a portion of one or more of a mask, a collar, a mouthpiece, or the like. As examples of masks, these could be provided in the form of a domino mask, ski mask, or other common mask; in the form of pads/patches covering all or some of the cheeks, chin, upper lip, nose, forehead, or other portions of the head and/or neck; or in the form of a cap/helmet masking portions of the head away from the face and neck (and perhaps masking portions of the face and/or neck as well). Collars could take the form of (for example) sleeves/bands covering some or all of the neck, and/or some or all of the forehead, or a portion of the face. As examples of mouthpieces, these might be provided in the form of a retainer, a mouthguard, or the like. Thus, such a device might simply be put on by a patient for wear during exercises, without the need for intrusive measures or other burdensome or painful procedures.

Stimulation is preferably generated by a pattern generator which delivers stimulation (e.g., electrical pulses) in a random pattern, or in a repeating pattern such as brief pulses provided at a regular frequency. It is notable that the stimulation pattern need not, and preferably does not, rely on any feedback from the patient and/or the patient's surroundings—for example, the stimulation pattern need not be varied if the patient is monitored and it is determined that the patient is having difficulty with the task (or conversely if the patient is performing the task well). Thus, the pattern generator can simply be set to a random or predetermined pattern by a therapist or by the patient, and the stimulators can continue to deliver this same preset pattern as the patient performs the task (and for any post-task stimulation period thereafter). The pulses are preferably delivered to the patient above the patient's threshold of sensory perception (i.e., such that the patient can feel them), but below the level of discomfort. However, it is believed that the invention may also yield results if the pulses are delivered to the patient just below the patient's threshold of perception (i.e., such that the patient does not notice them, at least unless the patient concentrates on feeling them).

It has been found that improvement in patients' abilities seems to be best effected if the following methodology is followed. Initially, while stimulation is supplied to the patient, the patient is made to perform the difficult task (one hindered by neural impairment) at low intensity. This is believed to provide the patient with confidence and proficiency, and can be performed for a short time period (e.g., for 5 minutes). The patient is then made to perform the task at high intensity, preferably at the limit of their ability, in conjunction with stimulation. Assistance can be provided if needed, and this step can also be performed for a short time period (e.g., for 5 minutes). The patient then performs the task at moderate intensity in conjunction with stimulation, again for a short time period (e.g., for 5 minutes). Finally, after a short rest, the patient might undergo a period of stimulation (e.g., for 20 minutes) during which the task is again performed at moderate intensity. This routine is preferably performed twice per day, with a span of about four hours separating the sessions. It is also notable that the invention also appears to improve cognition and mood in at least some cases, i.e., the invention may also be useful for treatment of conditions such as learning, attention, and/or memory disorders (e.g., Alzheimer's disease, attention deficit disorder, etc.), as well as mood disorders (e.g., depression, post-traumatic stress disorder, obsessive-compulsive disorder, etc.).

In one aspect, the invention features a method for non-invasively assisting neurorehabilitation in a patient. The method includes engaging a patient in a cognitive exercise wherein the patient's ability to perform the cognitive exercise is hindered by impairment of the patient's nervous system. The method also includes simultaneously providing intraoral cutaneous stimulation of at least one of the patient's trigeminal nerve or the patient's facial nerve via one or more stimulators situated within the patient's mouth.

In some embodiments, the method also includes providing intraoral cutaneous stimulation via one or more stimulators situated within the patient's mouth synchronously with the patient's engagement in the cognitive exercise. In some embodiments, the method also includes providing the intraoral stimulation to the patient's tongue. In some embodiments, the method also includes engaging a patient in a cognitive exercise wherein the patient's ability to perform the cognitive exercise is hindered by tinnitus.

In another aspect, the invention features a method for assisting non-invasive neurorehabilitation in a patient. The method includes delivering non-invasive cranial nerve stimulation to the patient. The method also includes regulating energy of the stimulation delivered to the patient. The method also includes controlling stimuli according to a desired neurologic outcome.

In some embodiments, the method also includes stimulating at least one of the patient's vision, hearing, vestibular systems, or somatosensory systems. In some embodiments, the method also includes synchronously stimulating at least one of the patient's vision, hearing, vestibular systems, or somatosensory systems. In some embodiments, the method also includes nonsynchronously stimulating at least one of the patient's vision, hearing, vestibular systems, or somatosensory systems. In some embodiments, the method also includes synchronously stimulating at least one of the patient's vision, hearing, vestibular systems, or somatosensory systems. In some embodiments, the method also includes synchronously stimulating the patient's hearing to effect treatment of tinnitus. In some embodiments, the method also includes delivering non-invasive cranial nerve stimulation to the patient to effect the treatment of one or more neurological disorders including traumatic brain injury, stroke, loss of cerebral blood flow, chemical brain injury, depression, obsessive-compulsive disorder, bipolar disorder, schizophrenia, vestibular deficits, Parkinson's disease, multiple sclerosis, essential tremor, autism, dyslexia, memory disorders, information processing disorders, traumatic amputation, reflex sympathetic neuropathy, a disorder affecting sleep patterns (e.g., insomnia), tinnitus, emotional dysregulation, and post-traumatic stress disorder. In some embodiments, the method also includes delivering non-invasive cranial nerve stimulation to the patient to effect the improvement of at least one of athletic performance, musical performance, vehicle operation, or general coordination.

In yet another aspect, the invention features a method for assisting neurorehabilitation of a patient to effect treatment of tinnitus. The method includes delivering neuromodulation to the patient's intraoral cavity with at least one of actuators or transducers. The method also includes simultaneously delivering auditory stimulation to the patient with the at least one of actuators or transducers.

In yet another aspect, the invention features a system for delivering neuromodulation to a patient to effect the treatment of tinnitus. The system includes an electrode array configured to be situated in a patient's intraoral cavity for delivering neuromodulation to the patient's intraoral cavity. The system also includes a first transmission medium in electrical communication with the electrode array to conduct electrical signals to the plurality of electrodes. The system also includes at least one transducer for delivering auditory stimulation to the patient simultaneously or sequentially with the delivery of neuromodulation to the patient's intraoral cavity. The system also includes a second transmission medium in electrical communication with the at least one transducer to conduct electrical signals to the at least one transducer. The system also includes control electronics providing electrical signals via the first and second transmission medium to the electrode array and the at least one transducer.

In yet another aspect, the invention features a system for delivering neuromodulation to a patient's intraoral cavity. The system includes a u-shaped, generally cylindrical member configured to be positioned below a patient's tongue in the patient's intraoral cavity. The system also includes a plurality of electrodes embedded along an upper surface of the u-shaped member. The system also includes a transmission medium attached to an anterior apex of the u-shaped cylindrical member for conducting electrical signals to the plurality of electrodes. The system also includes control electronics providing electrical signals via the transmission medium to the plurality of electrodes.

In some embodiments, the plurality of electrodes is configured to stimulate the sublingual branch of the trigeminal nerve and avoids excitation of an inferior aspect of the tongue. In some embodiments, the electrodes are circular, having a diameter in the range of 1-10 millimeters. In some embodiments, the electrodes are composed of at least one of gold, titanium, platinum, stainless steel, or conductive polymer. In some embodiments, the system also includes a conductive polymer material, the conductive polymer material located between the electrodes and the patient to provide a uniform current density, thereby preventing localized high currents. In some embodiments, the system also includes electronics providing electrical signals having a temporally modulated intensity. In some embodiments, the electrical signals have a temporally modulated current or voltage. In some embodiments, the system also includes electronics providing electrical signals having a temporally modulated pulse structure. In some embodiments, the electrical signals have a temporally modulated frequency, pulse grouping, or bursts. In some embodiments, the system also includes electronics providing electrical signals having a spatially modulated pattern. In some embodiments, the system also includes electronics providing electrical signals that are both spatially and temporally modulated.

In yet another aspect, the invention features a system for delivering neuromodulation to a patient's intraoral cavity. The system includes a curved member shaped to accommodate an anterior portion of the patient's tongue. The system also includes a plurality of electrodes embedded along an upper surface of the curved member. The system also includes a bite bar located adjacent to the curved member for accommodating the patient's teeth. The system also includes control electronics for delivering electrical signals to the plurality electrodes, the control electronics being attached to the curved member and shaped to accommodate the patient's lips.

In some embodiments, the plurality of electrodes is configured to stimulate the cranial nerves located at the apex of the patients tongue. In some embodiments, the electrodes are circular, having a diameter in the range of 1-10 millimeters. In some embodiments, the electrodes are composed of at least one of gold, titanium, platinum, stainless steel, or conductive polymer. In some embodiments, the system also includes a conductive polymer material, the conductive polymer material located between the electrodes and the patient to provide a uniform current density, thereby preventing localized high currents. In some embodiments, the system also includes control electronics providing electrical signals having a temporally modulated current or voltage. In some embodiments, the system also includes control electronics providing electrical signals having a temporally modulated pulse structure. In some embodiments, the electrical signals have a temporally modulated frequency, pulse grouping, or bursts. In some embodiments, the system also includes control electronics providing electrical signals having a spatially modulated pattern. In some embodiments, the system also includes control electronics providing electrical signals that are both spatially and temporally modulated.

In yet another aspect, the invention features a method for assisting neurorehabilitation of a patient. The method includes providing stimulation of the patient's cranial nerves via actuators or transducers. The method also includes receiving physiological information about the patient's response to the stimulation. The method also includes controlling the stimulation energy delivered to the actuators or transducers. The method also includes synchronizing the stimulation provided to the actuators or transducers. The method also includes controlling the spatial and temporal pattern of the stimulation delivered to the patient via the actuators or transducers. The method also includes adjusting the stimulation parameters during neurorehabilitation of the patient, based on the received physiological information.

In some embodiments, the method includes receiving information about the patient's environment and adjusting the stimulation parameters during the neurorehabilitation of the patient, based on the information about the patient's environment.

In yet another aspect, the invention features a method for non-invasively assisting neurorehabilitation in a patient comprising. The method includes engaging the patient in a physical movement wherein the patient's ability to perform the physical movement is hindered by impairment of the patient's nervous system. The method also includes providing intraoral cutaneous stimulation of at least one of the patient's trigeminal nerve or the patient's facial nerve via one or more stimulators situated within the patient's mouth.

In some embodiments, the method also includes providing intraoral cutaneous stimulation electrically via an electrode array situated within the patient's mouth synchronously with the patient's engagement in the physical movement.

In yet another aspect, the invention features a headband for delivering cranial non-invasive neuromodulation to a patient. The headband includes a plurality of electrodes configured to contact a region of the patient's skin over the facial and trigeminal ganglia, the plurality of electrodes configured to deliver electrical pulses to the patient to stimulate one or more of the patient's trigeminal and facial nerve. The headband also includes a band connected to the plurality of electrodes and traversing the length of the patient's head.

Further advantages, features, and objects of the invention will be apparent from the remainder of this document in conjunction with the associated drawings.

DETAILED DESCRIPTION OF PREFERRED VERSIONS OF THE INVENTION

Figure 1:
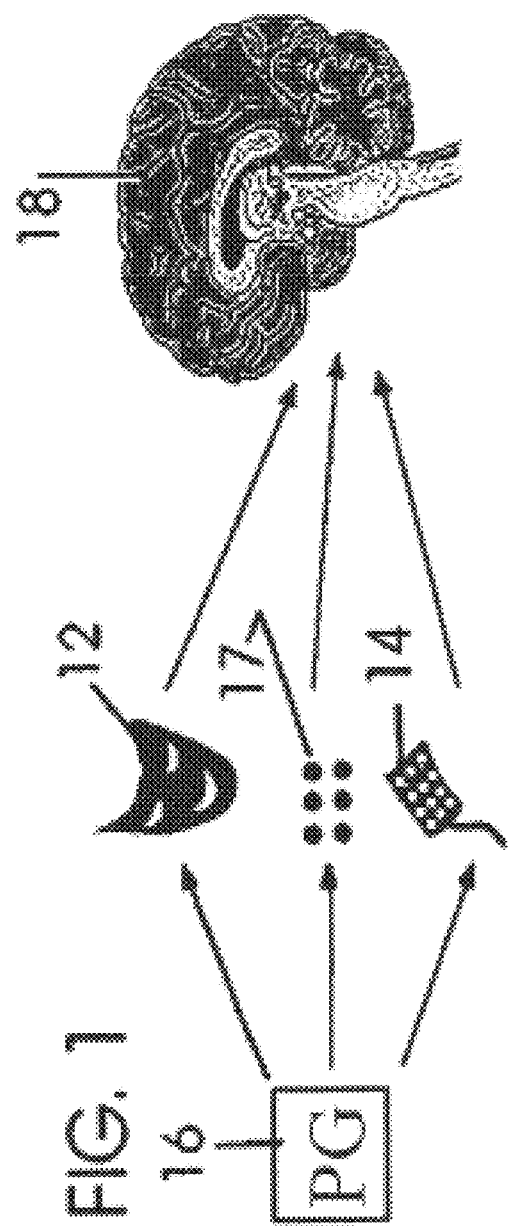
FIG. 1 is a simplified signal flow chart of an exemplary version of the invention wherein stimulation is applied to a patient independently of any activity associated with a brain dysfunction or other neural impairment.

To expand on the discussion above, FIG. 1 illustrates an exemplary version of the invention wherein a facial mask 12 or tongue plate 14 bears a set of spatially arrayed electrical, mechanical, thermal, electromagnetic, or other stimulators 17, such as electrodes. These stimulators 17 preferably provide stimulation to the trigeminal nerve or subportions thereof, e.g., to the lingual nerve, and thereby stimulate the brain. Such stimulation is preferably non-invasive, that is, in distinction from brain-penetrating electrodes or other matter which penetrates or otherwise modifies the flesh, and is most preferably cutaneous (i.e., effected by stimulators 17 which simply rest in contact with the skin).

The facial mask 12 or tongue plate 14 may communicate with a pattern generator 16 to energize the stimulators to stimulate the brain 18. The pattern generator 16 may generate a regular or random stimulation pattern independent of the environment or other sensory input to, or response by, the patient.

Figure 2:
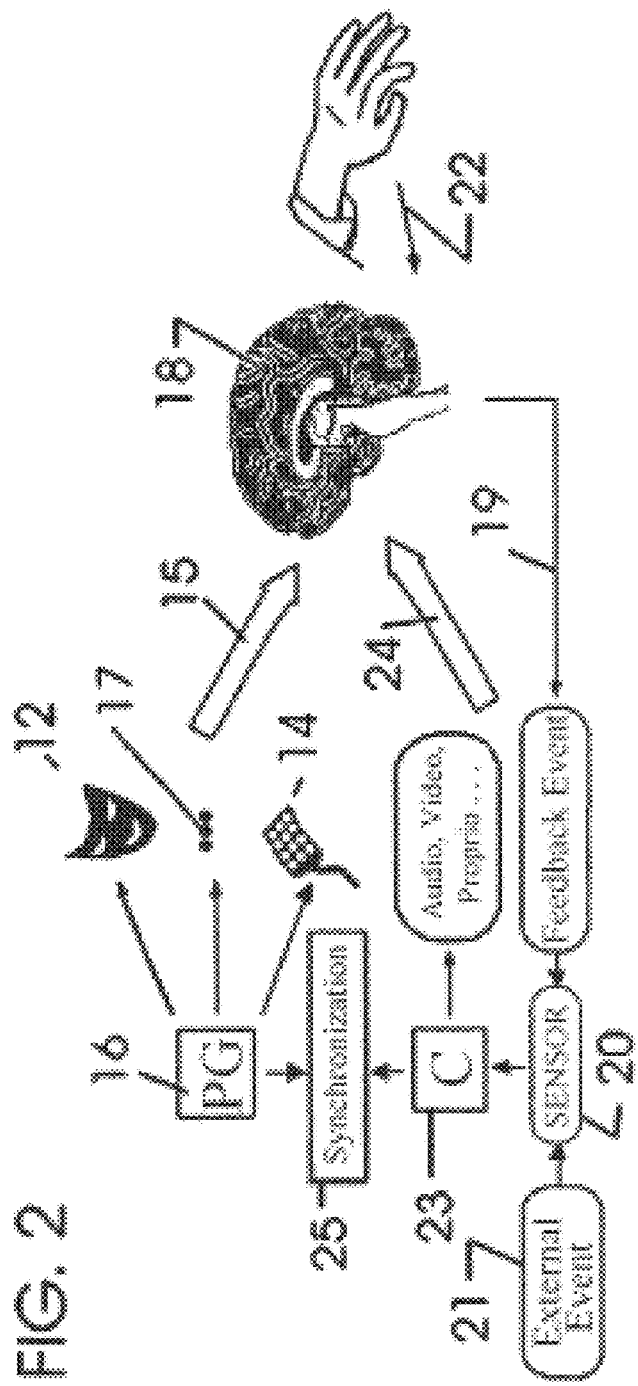
FIG. 2 is a simplified signal flow chart similar to that of FIG. 1 in which the stimulation is synchronized with an activity and/or external stimuli related to the neural impairment.

FIG. 2 illustrates an alternative version of the invention wherein the device may provide feedback 19 from a sensor 20, for example, a sensor monitoring a patient activity such as movement of a limb or the like. The sensor 20 may also or alternatively monitor an external event 21 related to the environment and possibly related to patient activity, for example, describing a lever that the patient must grasp. The output of the sensor 20 may be received by a controller 23 that may provide an audio, video or other sensory signal 24 back to the patient, for example, so that the patient might better know the status of his/her performance of the activity. The controller 23 may also synchronize the pattern generator 16 with the external signal 21 or feedback signal 19 as indicated by process block 25 so that the stimulation may be linked to particular activities by the patient or stimuli from the external environment, for example, if it appears that the patient's performance is substandard. The patient activity generating the feedback signal 19 and the external signal 21 is preferably related to the neural pathways to be rehabilitated. For example, the feedback signal 19 may measure a muscular tremor related to impairment such as Parkinson's disease, multiple sclerosis, autism, Alzheimer's disease, vertigo, depression, or a disorder affecting sleep patterns (e.g., insomnia). It is believed that this non-invasive neuromodulation 15, together with the sensory signals 24 from the activity itself, primes or up regulates those neurons of the brain 18 associated with the activity 22 and thereby encourages a therapeutic rehabilitation of the affected areas of the brain 18.

Figure 3:
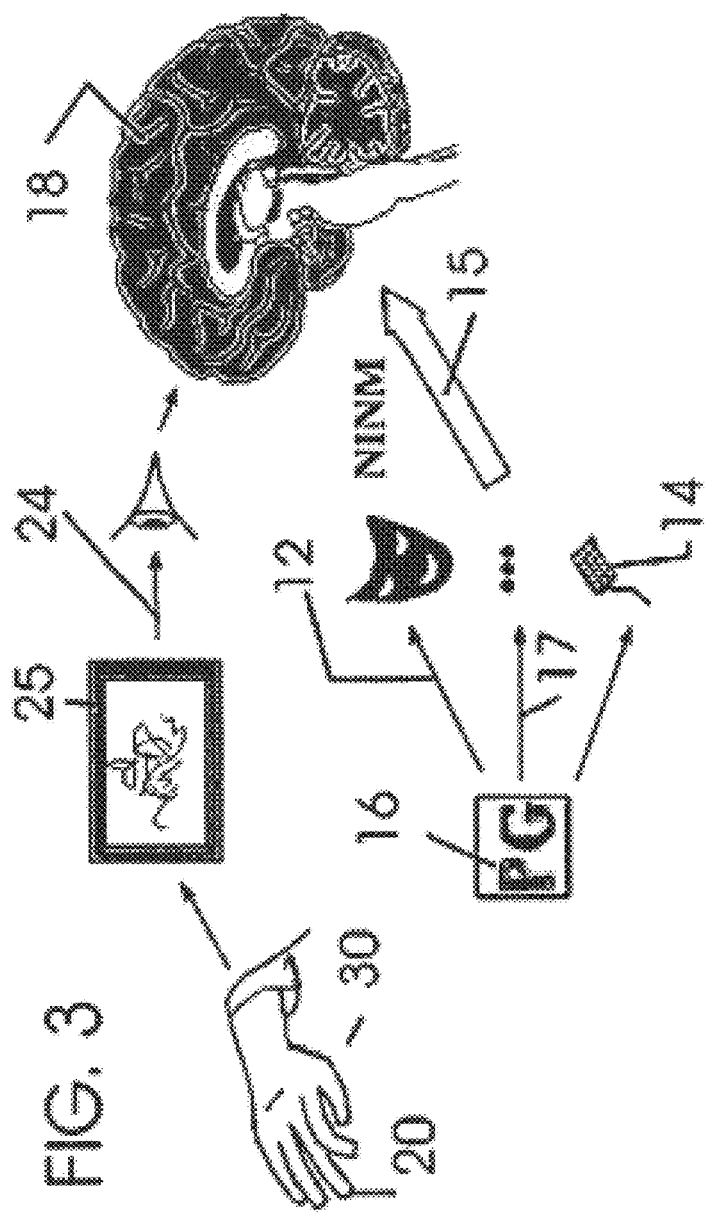
FIG. 3 is a simplified signal flow chart similar to that of FIG. 1 wherein the stimulation is simply contemporaneous with an activity associated with the neural impairment.

FIG. 3 shows another exemplary version of the invention wherein the stimulation of the non-invasive neuromodulation 15 is independent from and unsynchronized with the sensory signals 24 produced by the activity 30, although it occurs contemporaneously with the activity 30. In this case the sensor 20 might, for example, be a finger cuff bearing accelerometers whose output is processed by a controller to provide sensory signals 24 (here a trajectory display on a terminal 25). At the same time, stimulation may be driven by the pattern generator 16 independently from the sensory signals 24. As noted previously, the therapeutic effects provided by the non-invasive neuromodulation 15 tend to continue after the non-invasive neuromodulation 15 ceases.

As previously noted, the pulses delivered by the stimulators can be random or repeating. The location of pulses can be varied across the stimulator array such that different stimulators are active at different times, and the duration and/or intensity of pulses may vary from stimulator to stimulator. It is believed that the nature of the pulses is not as important as the simple fact that the pulses are delivered during a task for which the patient wishes to improve his/her performance. The pulses therefore need not be delivered in dependence on any factors occurring outside the device during delivery of the electrical pulses, i.e., the pulses need not be delivered or varied in response to the quality of the patient's performance of the task. However, if desired, the pattern generator might receive feedback from the patient and/or the patient's environment, and might somehow modify pulse delivery in response. For example, more stimulation (e.g., pulse frequency and/or intensity) might be provided if it is detected that the patient's performance of the task is suffering rather than improving.

In practice, stimulation which delivers repeating pulses in the nature of a simple waveform, e.g., a square wave or series of regularly-spaced pulses, has been found to be effective. Also preferred are "bursts" of pulses which repeat at some frequency, with the pulses within the bursts repeating at a higher frequency (for example, as if the peaks or "on" periods of a square wave or other waveform were themselves formed of a series of pulses). The fundamental or harmonic frequency underlying the stimulation waveform may be chosen in dependence on the particular application. As examples, testing and/or inference suggest that the appropriate frequency for sensory dysfunction might be around 40 Hz; for Parkinson's disease, around 30-50 Hz; for involuntary movement/tremor, around 1-40 Hz; for voluntary movement coordination, around 50-100 Hz; for cognitive processes, around 100-300 Hz; for bradykinesia, around 150 Hz; for sleep or anesthesia, around 80 Hz; and for relaxation or wakefulness, around 0.5-2.0 Hz. In some applications, it may be most effective to have the delivery frequencies of certain electrodes (or other actuators/elements for delivering stimulation) differ in accordance with their location, e.g., electrodes in one area may deliver stimulation at one frequency and electrodes at another area deliver stimulation at another frequency (wherein the frequencies need not necessarily have a harmonic relationship).

As also previously noted, stimulation may be provided by electrical, mechanical, thermal, or electromagnetic actuators/elements, which may vary in their sizes and geometric configurations. Electrodes used in testing have typically been circular electrodes measuring between 1-10 mm in diameter, but electrodes may be differently sized and configured as desired. Cutaneous electrical stimulation of cranial nerve branches has been efficiently and inexpensively delivered using surface electrodes held gently against the skin or oral tissue using masks (including full or partial facial masks, e.g., patches or frameworks covering a portion of the face) and collars (including both neck collars and bands/sleeves fitting about portions of the head) which preferably situate the electrodes thereon to at least partially conform to the contours of the skin surface over which they are placed. The electrode material may be chosen to minimize corrosion and skin irritation, with possible electrode materials including gold, titanium, platinum, rhodium, and/or stainless steel. The electrode surface material may be full-thickness or a thin layer deposited by electroplating, vapor deposition, ion implantation, or similar processes. The electrode may be conductive, or possibly insulating so that only a capacitive displacement current flows into the skin. Insulating materials include various oxides of silicon, titanium, strontium, and/or tin, as well as various polymers such as polyester, polyimide, and/or polyamide-imide. Both mechanical and electrical contact between the electrode and skin may be further enhanced by the use of electrically conductive materials such as electrode gels (with or without conductive electrolytes) or distensible conductive polymers. Both gels and polymers may additionally have adhesive properties to further improve the electrode-skin interface. Exemplary materials of this nature are presently in common use for biopotential recording electrodes (e.g., for electrocardiography and electroencephalography), as well as for electrodes used for functional electrical stimulation (e.g. for neuromuscular stimulation or transcutaneous electric nerve stimulation for pain relief).

Where electrodes are used to deliver electrical stimulation, the pulses may be generated by oscillator/pulse generator circuits which deliver the desired frequency, voltage, current, power, or other electrical pulse property to the electrode-skin interface. Skin stimulation generally involves voltages of 10-500 volts and currents of 0.5-50 milliamps depending on factors such as electrode geometry and the location and condition of the site at which the electrode is to be placed. For oral tissue stimulation, similar currents but lower voltages of 1-40 volts may suffice. As previously noted, the stimulus waveform may have a variety of time-dependent forms, and for cutaneous electrical stimulation, pulse trains and bursts of pulses have been found useful. Where continuously supplied, pulses may be 1-500 microseconds long and repeat at rates from 1-1000 pulses/second. Where supplied in bursts, pulses may be grouped into bursts of 1-100 pulses/burst, with a burst rate of 1-100 bursts/second. A particularly effective cutaneous stimulus uses 25-50 microsecond pulses repeating at a rate of 200 pulses/second, with every fourth pulse omitted to yield a 3 pulse/burst structure that repeats at 50 bursts/second.

As briefly discussed earlier, mechanical stimulation (if used) may be delivered by various kinds of devices such as electromagnetic solenoids, shape-memory alloy (e.g. tin-nickel) actuators, piezoelectric actuators, electrically-active polymer actuators, electrorheological actuators, motors, electrostatic actuators, pneumatic or hydraulic cylinders or other devices, and micromechanical systems (MEMS) devices. The stimulation devices may be held against the skin by masks, collars, and other devices as described above for use with electrodes. Preferably, a mechanical actuator would be limited in size to agitate an area ranging between perhaps 1 square millimeter to 1 square centimeter of skin per actuator, but the size of the actuator (and thus the affected area) may be larger or smaller as necessary; for example, it is possible to construct a mechanical actuator that provides mechanical stimulation to an entire large skin area (e.g., the entire face) at once, as by using a vibrating rigid mask. The time dependency of mechanical stimulation is typically sinusoidal, with a rate of 1-1000 Hz and a displacement of 0.1 micrometer to 5 millimeters, but different stimulation waveforms/patterns may be used instead. A variation on mechanical stimulation is the use of high-frequency (0.1-10 megahertz) ultrasonic stimulation which may be modulated to produce a varying "wave pressure" mechanical stimulation of subcutaneous nervous system tissue.

It is believed that stimulation of the trigeminal nerve (the fifth cranial nerve or CN-V) or branches thereof provides particularly rapid and potent rehabilitative effect, though it is possible that stimulation of parts of the body other than the head and neck—and thus nerves other than the trigeminal nerve—might work suitably well. Stimulation of the tongue affects the lingual nerve, a branch of the mandibular nerve (CN-V3), one of the three major divisions of the trigeminal nerve. Cutaneosensory information delivered to the lower lip, chin, jaw, and lower cheek up to the sides of the scalp also affects the mandibular nerve. Another major division of the trigeminal nerve, the maxillary nerve (CN-V2), receives cutaneosensory information from the region of the upper lip, lateral aspect of the nose, upper cheeks, below the eyes, and the temples. The final division of the trigeminal nerve, the opthalmic nerve (CN-V1), receives cutaneosensory information from the upper anterior two-thirds of the upper scalp, and the anterior third of the face that includes the forehead, nose, and regions above the eyes.

Stimulation of the facial nerve (CN-VII) or branches thereof is also believed to be particularly beneficial, in part because such stimulation may provide antidromic (backward) stimulation of the facial nerve nucleus of the brainstem. Stimulation of the facial nerve can perhaps be most easily effected via stimulation of the oral cavity; for example, when stimulation is provided to the tongue via a mouthpiece, the facial nerve is effectively stimulated via the chorda tympani (taste nerve), a branch of the facial nerve. However, stimulation of other branches of the facial nerve might also be effected by use of one or more stimulators situated on masks, collars, or other devices which fit over all or a portion of the face, or other areas of the head and/or neck.

Other regions for which stimulation may be particularly effective include the back of the head, the dorsal part of the neck, and the middle of the shoulders. Stimulating these areas affects afferent nerves of the medial branches of the dorsal rami of the cervical spinal nerves (greater occipital—c2, occipital—c3, and c4-7, respectively). The areas above and behind the ear (lesser occipital—c2,3), below the ear (greater auricular—also c2,3), the anterior neck (transverse cervical—also c2,3), and beneath the jaw and chin (supraclavicular—c3,4) can also be useful.

A preferred methodology for therapeutically administering the invention is briefly described above, and is now discussed in greater detail. It should be understood that this methodology is merely one which has proven effective in preliminary testing, and that variations from this methodology are possible, and are regarded as being encompassed by the invention. The following steps of the methodology are preferably performed in the order presented below.

Initially, the patient is preferably queried to assess current health and functional state (emotional, physical and cognitive). This may include an oral interview and/or testing, and known and conventional interviews/tests such as the Short Form-36 (SF-36, for general evaluation of physical and mental health), the Continuous Cognitive Performance Test (for measuring cognition/attention), the Hamilton Depression Scale (HAM-D, for measuring depression severity), the Dynamic Gait Index (for measuring gait and the likelihood of falling), the Dizziness Handicap Index (DHI, for measuring the severity of vestibular disorders), the Activities-specific Balance Confidence Scale (ABC, for measuring fear of falling), the Multiple Sclerosis Impact Scale (MSIS, for measuring the severity of symptoms of multiple sclerosis), and/or other tools may be employed.

The patient may then be educated about the global, daily, and session-specific objectives of the therapy. This may include familiarization with the stimulation routine, hardware, and software to be used in the therapy. This can help to alleviate patient anxiety, and increase cooperation and confidence.

The patient is then preferably physically conditioned within the limits of the patient's (initial) ability, without any stimulation being applied, wherein the conditioning at least partially encompasses actions which are hindered by the patient's functional deficit. This can be useful to familiarize the patient with the planned therapy for the day; to redevelop body awareness of potential ability and of unconscious adaptations the patient may have made; and to give the therapist an estimation of the patient's degree of (and confidence in their) brain-body integration.

The patient may then be made to engage in a short (e.g., 5-minute) therapy period wherein the patient performs one or more tasks selected to address the patient's functional deficit (i.e., tasks which are hindered by the patient's functional deficit), with the tasks being performed at a low intensity level while the patient simultaneously receives stimulation. The task intensity is set at a low level to better familiarize the patient with the routine they will be experiencing during the remainder of the therapy session. This step helps build familiarity with a task, and establishes confidence in task performance. This step may be followed by a short (e.g., 3-minute) rest period.

The patient then preferably engages in a short (e.g., 5-minute) therapy period wherein the patient performs the same task while receiving stimulation, with the task being modified to present a challenge that is slightly beyond the patient's current functional capacity. The high-intensity challenge may require active reinforcement and redirection by the therapist to ensure the patient performs the task correctly under new operating conditions, and that the patient does not (for example) rely on compensatory strategies that the patient established in response to the functional deficit. This step may be followed by a short (e.g., 3-minute) rest period.

The patient can then engage in a short (e.g., 5-minute) therapy period wherein the patient again performs the same task while receiving stimulation, with the task now being modified to present a moderate challenge that is within the patient's current functional capacity. This familiarizes the patient with the moderate-intensity task. This step may be followed by a short (e.g., 3-minute) rest period.

The patient then preferably engages in a longer therapy period (e.g., 20 minutes) at the same moderate level, with the patient simultaneously receiving stimulation. This period allows for a longer period during which neural plasticity and rehabilitation is induced in the neural structures involved in performing the particular task.

Optionally, stimulation might then be applied (or continued) for a brief period of time while the patient is not engaged in the task. This may be useful to continue stimulation of the neural structures involved in performing the particular task (though other neural structures may be stimulated as well), and may help to enhance rehabilitation.

The patient may then engage in simplified post-therapy querying and assessment using metrics which are the same as or similar to those noted above. This helps to quantify changes in functional capacity, and to assess the need for changes in the rate and type of therapy progression. No stimulation need be applied during this step.

These steps are preferably performed by a patient at least twice per day, with a period of at least 4 hours separating each session (i.e., each set of steps). If more than one session is performed per day, some of the steps (e.g., the first and second steps) might be omitted for the sessions following the first one.

It is believed that the benefits of the invention are not limited to neurorehabilitation to at least partially restore impaired movement or physical function, and that the benefits extend to other human capabilities that depend on neurological function. In particular, it is believed that the benefits of the invention extend to at least partial restoration of mental capabilities as well as physical capabilities. For example, rehabilitation of impaired cognitive (e.g. attention, memory, learning, multitasking, etc.) function may be improved by providing stimulation during tasks designed to exercise perceptual and cognitive skills. Such tasks could include commonly available "brain-training" exercises or games, e.g., computerized or non-computerized exercises or games designed to require use of attention span, memory/recollection, reading comprehension, etc. For example, a patient with memory impairment due to Alzheimer's disease might perform a set of memory exercises of progressively greater difficulty in conjunction with stimulation, thereby functionally and structurally improving memory circuitries via induced synaptic plasticity. Beneficially, mental exercises of this nature can be readily delivered to a patient via computer (as in the nature of tests, puzzles, or other queries directed to the patient via a computer screen or other output device), with the computer collecting the patient's responses, thereby reducing the need for (and expense of) therapist involvement. Because the benefits of stimulation are not specific to any particular disease mechanism, they may be beneficial for a wide range of degenerative, traumatic, or degenerative causes of cognitive impairment, including (but not limited to) Parkinson's disease, multiple sclerosis, stroke, head trauma, autism and cerebral palsy.

As another example, it is believed that the invention can provide benefits for at least some type of mood disorders, e.g. depression, anxiety, bipolar disorder, schizophrenia, post-traumatic stress disorder, obsessive-compulsive disorder, etc. In these cases, the tasks performed by the patient might include those that are commonly used during therapies for mood disorders, e.g. cognitive-behavioral therapy exercises, progressive exposure to "triggers" for compulsive behaviors, visualization exercises, meditation, relaxation techniques, etc. Here too stimulation may enhance functional and structural plastic changes associated with the therapeutic task, causing the new behaviors practiced during the therapy to become more automatic.

It is further believed that the invention can also assist in the enhancement of nonimpaired physical and/or mental capabilities, as well as assisting in at least partial restoration of impaired physical and/or mental capabilities. Thus, the invention might assist with proficiency in physical and/or mental activities such as sports activities, reading/studying, playing of a musical instrument, etc. in "patients" who do not have any recognized impairment in these fields. As for patients having impaired neurological states, the combination of stimulation and practicing the particular task (physical, cognitive or psychological) will enhance the plastic learning response of the areas and systems of the brain engaged in performance of that task.

It is also emphasized that the application of stimulation is believed to be beneficial where the stimulation is applied prior to and/or after performance of tasks, as well as during performance of such tasks. Application of stimulation before, during, and/or after any task will potentially enhance the efficiency (and efficacy) of neural circuitries responsible for performance of that task, by changing the neuro-chemical environment, the physical structure, and/or other physiological aspects of these neural circuitries. For example, stimulation before the task may create chemical changes that prime the neural tissue to be more receptive to plastic changes; stimulation during the task may increase the baseline neural activity to enhance the plastic response to task performance; and stimulation after the task may enhance consolidation of structural and functional changes related to the task.

Figure 4:
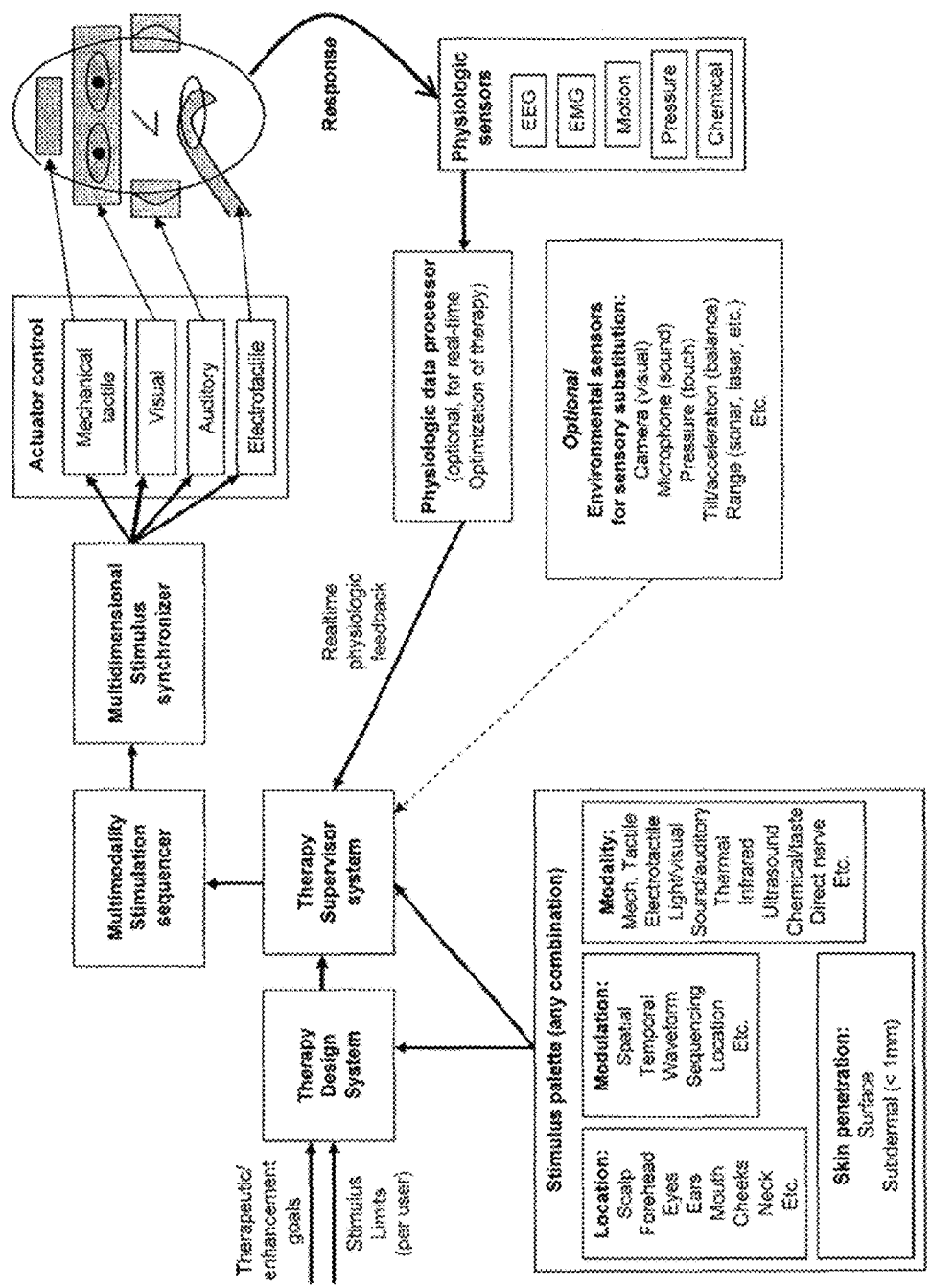
FIG. 4 is a diagram showing an NINM system in accordance with an illustrative embodiment of the invention.

In one embodiment, an NINM system 400 comprises several components as illustrated in FIG. 4. The NINM system 400 includes a therapy design system 405, a therapy supervisor system 410, a multimodality stimulation sequencer 415, a multidimensional stimulus synchronizer 420, actuator control subsystem 425, and a stimulus palette 445. In some embodiments, the NINM system 400 includes physiologic sensors 430. In some embodiments, the NINM system 400 includes a physiologic data processor 435. In some embodiments, the NINM system 400 includes environmental sensors 440.

The therapy design system 405 provides the targeted set of stimulation parameters, subject to therapeutic and/or enhancement goals, individual characteristics of the user, and available stimulus parameters. The stimulation parameters can be chosen to stimulate any combination of the scalp, forehead, eyes, ears, mouth, cheeks and/or neck. The stimulation can be any combination of spatial stimulation or temporal stimulation. The stimulation can be achieved by any combination of mechanical tactile stimulation, electrotactile stimulation, light/visual stimulation, sound/auditory stimulation, thermal stimulation, infrared stimulation, ultrasound stimulation, chemical/taste stimulation, and/or direct nerve stimulation. The therapy supervisor system 410 provides real-time control of the stimulation parameters (e.g., waveform, intensity, frequency, wavelength, pitch, etc.) in response to the therapeutic or enhancement goals, available stimulus combinations (e.g., palette), and real-time data from physiologic sensors that monitor the state of the user. The therapy supervisor system can optionally use data from environmental sensors 440 if the NINM system is combined with sensory substitution. The multimodality stimulation sequencer 415 controls the spatial and temporal patterns of the various modalities and locations of stimuli according to the desired neurologic outcome (e.g., brain activity). The multidimensional stimulus synchronizer 420 provides the designed timing relationship between the various modalities and locations of stimuli. The actuator control subsystem 425 provides control of energy (e.g., electrical) to the actuators on the user. The actuators can provide visual stimulation, audio stimulation, electrotactile stimulation, mechanical tactile stimulation, or any combination thereof. The audio stimulation can be delivered to the patient by an auditory stimulation system using sound emitting devices. The audio and/or visual stimulation can be spatially or temporally modulated. The user 426 receives stimulation of the cranial nerves via actuators or transducers that stimulate the sensory channels (e.g., tactile, visual, or auditory channels). In some embodiments, the user receives stimulation of non-cranial nerves. In some embodiments, the user receives artificial kinds of stimulation that can directly stimulate the cranial nerves, bypassing the specialized end-receptors. For example, the artificial kinds of stimulation can be electrical, ultrasound, or infrared. The stimulus palette 445 provides the range of possible stimulus parameters in all possible combinations of location, modulation, modality and skin penetration. In some embodiments, the physiologic sensors provide information about the state of the user and the user's response to the efficacious therapeutic and/or enhancement stimulation. In some embodiments, the physiologic data processor extracts the relevant components of the user physiologic data that can be used by the therapy supervisor system to effect real-time, closed-loop control of the stimulation. In engineering control system nomenclature it can be called an observer. In some embodiments, the environmental sensors provide information about the environment, external to the subject. If used, the environmental sensors effect sensory substitution or sensory augmentation, which can enhance the base efficacy of NINM.

Figure 5:
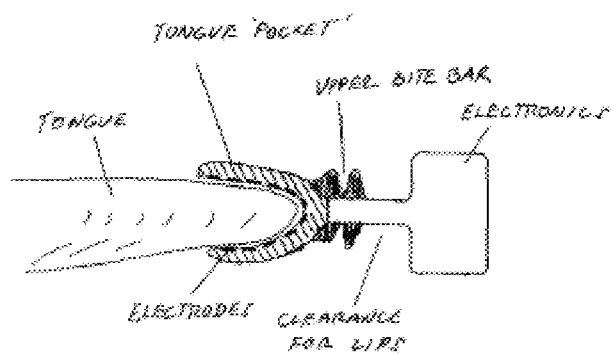
FIG. 5 is a diagram showing a tongue-tip stimulator in accordance with an illustrative embodiment of the invention.

In one embodiment, an NINM system is realized by employing a tongue-tip stimulator 500 as shown in FIG. 5. The tongue-tip stimulator 500 includes a tongue pocket 505, a bite bar 510, and electronics 515. The tongue pocket 505 includes electrodes 520. The tongue pocket 505 covers the tip of the tongue. During operation, a user bites down on the bite bar 510 and places his/her tongue in contact with the tongue pocket 505. The electronics 515 deliver electrical signals to the electrodes 520, stimulating the tip of the tongue. In some embodiments, the tongue pocket stimulates the top, bottom, tip, and/or side surfaces of the tongue.

Figure 6:
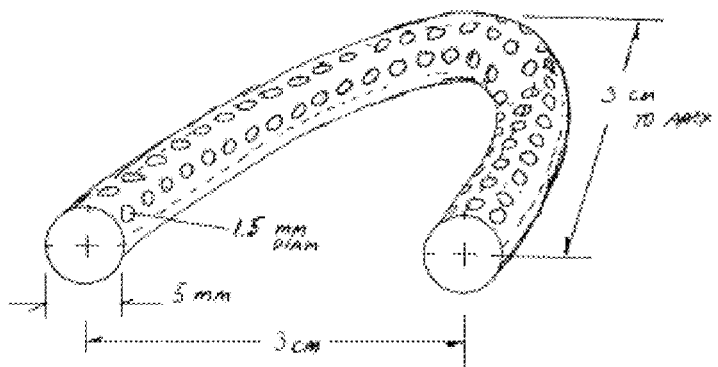
FIG. 6 is a diagram showing a "U" shaped electrode array in accordance with an illustrative embodiment of the invention.

In one embodiment, an NINM system is realized by employing a "U" shaped electrode array 600 as shown in FIG. 6. The "U" shaped electrode array 600 includes hemi-circumferential bands of electrodes 605 embedded in a cylindrical flexible polymer substrate 610. In some embodiments, the "U" shaped electrode array 600 includes at least 100 hemi-circumferential bands. In some embodiments, the length of the "U" shaped electrode array is approximately 3 cm. In some embodiments, the width of the "U" shaped electrode array is approximately 3 cm. In some embodiments, the diameter of the "U" shaped electrode array is approximately 5 mm. In some embodiments, the electrodes are approximately 1.5 mm in diameter.

During operation, a user places the "U" shaped electrode array 600 in his/her mouth below the tongue. The array is designed to selectively stimulate the sensory fibers in the sublingual branch of the Trigeminal Cranial Nerve (CN-V), and avoid excitation of the superficial muscles on the inferior aspect of the tongue. In some embodiments, the required circuitry, including a stimulation source is included in the center of the "U" shaped electrode array 600. In some embodiments, the "U" shaped electrode array 600 stimulates the sensory fibers of the sublingual branch of the trigeminal nerve, while avoiding excitation of the superficial muscles on the inferior aspect of the tongue. In some embodiments, a small multi-stranded ribbon cable that conducts electrical signals to the electrodes exits the mouth at the anterior apex of the "U" shaped array 600. The cable is then connected to a stimulation source. The stimulation source can provide amplitude modulated trains of voltage pulses to each electrode in a predetermined spatio-temporal pattern to elicit the desired afferent sensorineural activity in the sensory fibers of the trigeminal nerve. The pattern of the electrotactile stimulation is produced by a stimulus sequencer and synthesizer program running on a host PC. The ensemble afferent pathways conduct the resulting trains of neural impulses to the trigeminal nucleus and adjacent structures in the brainstem that are responsible for sensory-motor and homeostatic regulation. Sustained presentation of the stimulation for a time duration in the range of 12 to 25 minutes can effects changes in brain activity consistent with neuromodulation. In some embodiments, an electrode array is shaped to conform to the space between the gums and the lips, stimulating both regions.

Figure 7:
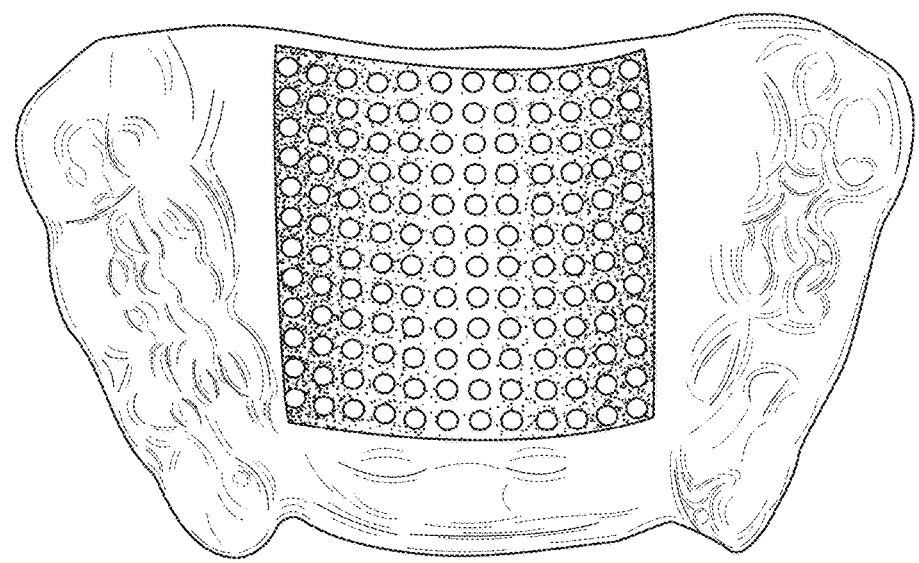
FIG. 7 is a diagram showing a retainer-like structure in accordance with an illustrative embodiment of the invention.

FIG. 7 shows a retainer-like structure 700 having a plurality of electrodes 705, a tooth conforming surface 710, and internal electronics. During operation, a patient can insert the retainer-like structure into his/her mouth with the patient's teeth contacting the tooth conforming surface 710. The internal electronics can deliver electrical pulses to the plurality of electrodes 705 to effect non-invasive neuromodulation through stimulation of the patient's trigeminal and/or facial nerve.

Figure 8A:
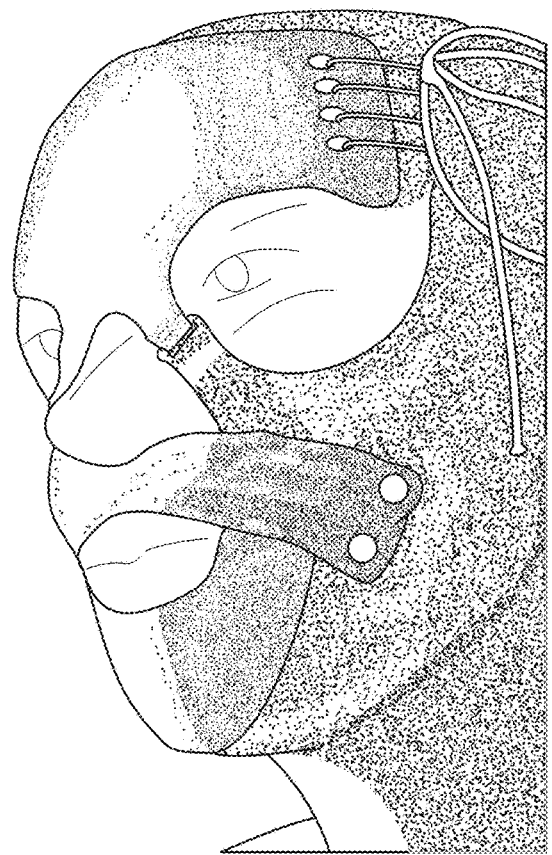
FIGS. 8A-8E are diagrams showing various face masks in accordance with illustrative embodiments of the invention.
Figure 8B:
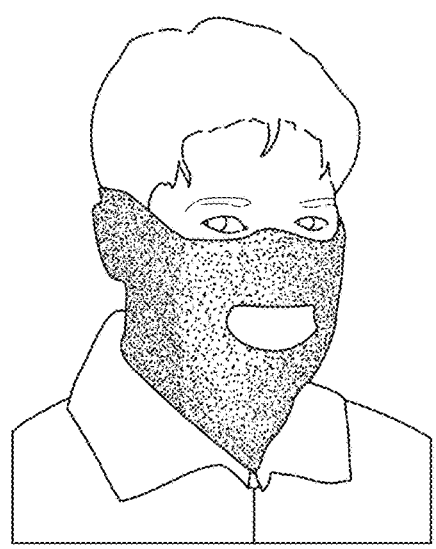
Figure 8C:
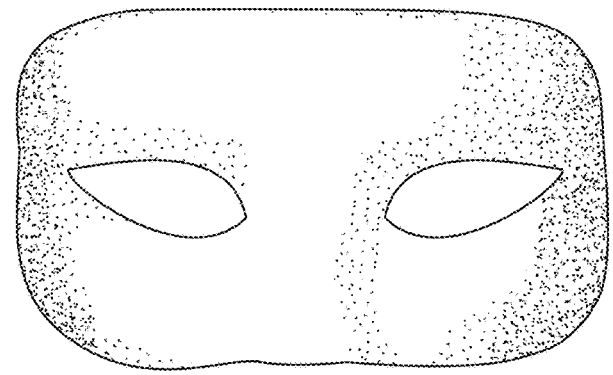
Figure 8D:
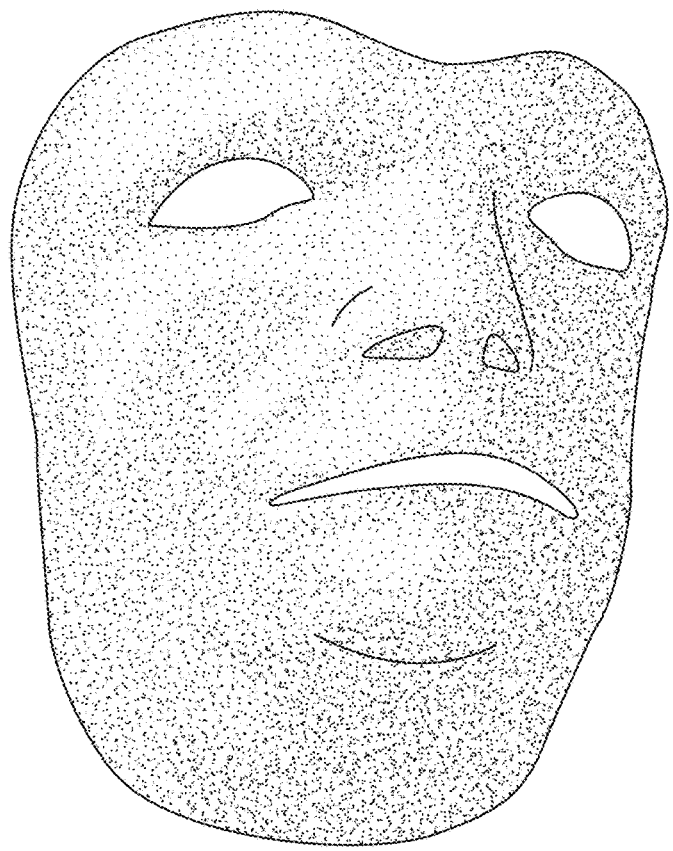
Figure 8E:
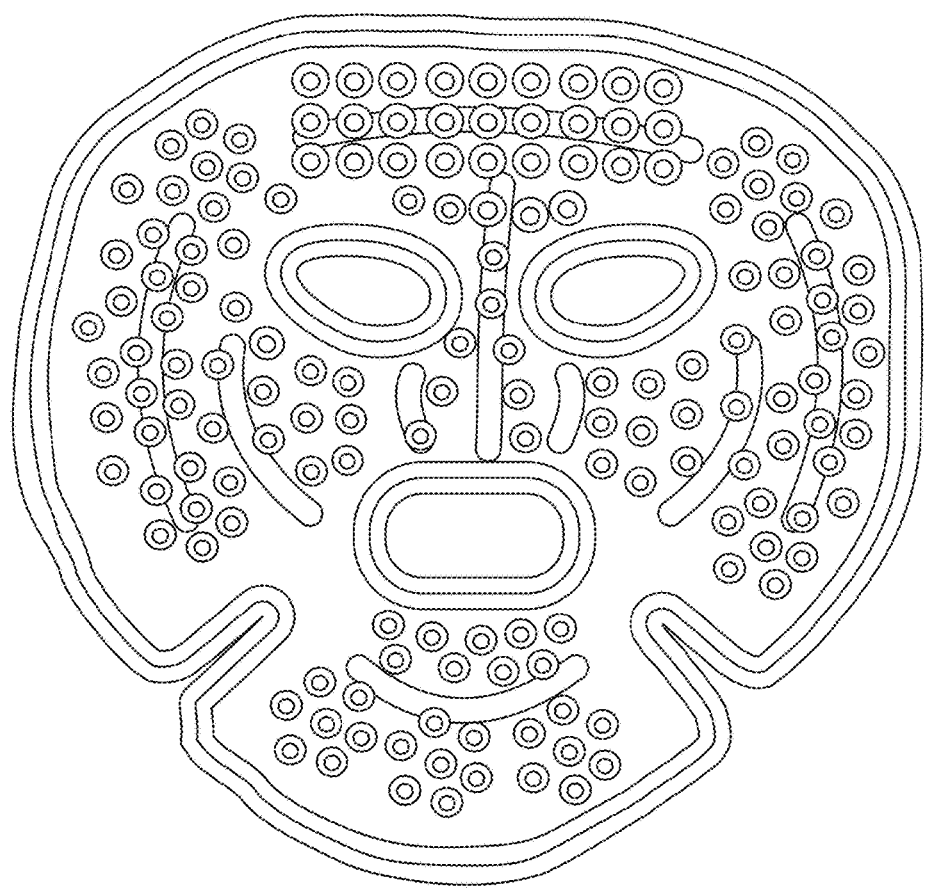

FIGS. 8A-8E show various face masks that can be used to deliver non-invasive neuromodulation stimuli to a patient. FIG. 8A shows a full flexible face mask covering exposed skin from the neck up. FIG. 8B shows a flexible collar covering a patient's neck and chin region. FIG. 8C shows a mask that covers the temple region surrounding the patient's eyes. In some embodiments, the mask shown in FIG. 8C can be flexible or rigid. FIG. 8D shows a rigid face mask that is custom fitted to the patient's face. FIG. 8E shows a conformal mask insert with electrodes for electrotactile stimulation. For each of the masks shown in FIGS. 8A-8E, stimulators can be integrated into the mask itself (e.g., using conductive polymers or conductive/wired textiles) or can be a separate conformable sheet containing the stimulators, fitted between the mask and the skin. Stimulation can be provided as electrical, mechanical or thermal excitation of the sensory fibers in the skin adjacent to the tactor.

Figure 9:
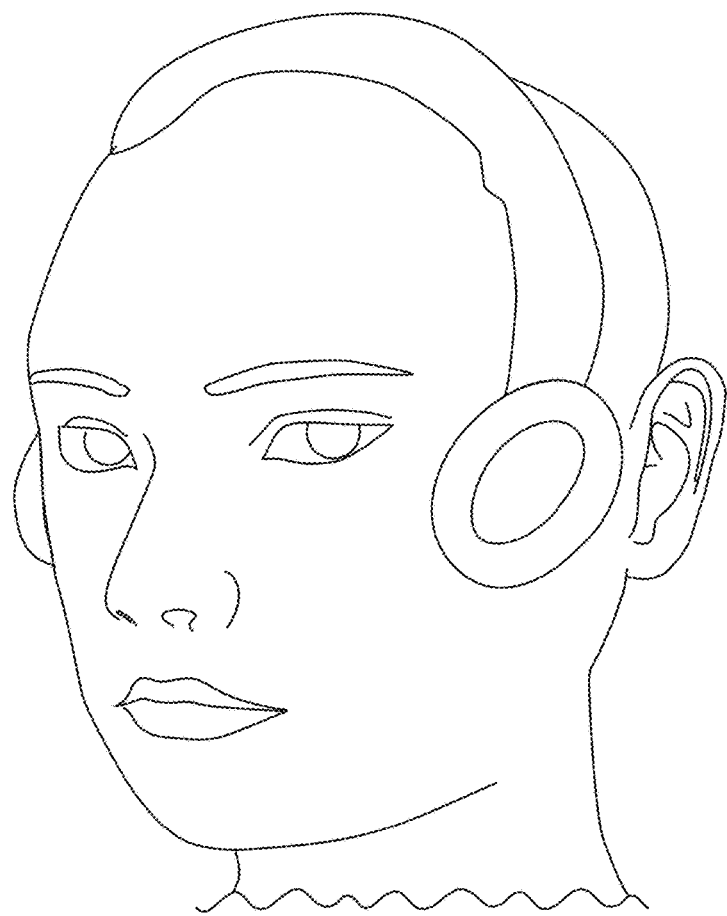
FIG. 9 is a diagram showing a headband in accordance with an illustrative embodiment of the invention.

FIG. 9 shows a headband 905 for delivering cranial nerve non-invasive neuromodulation. The headband 905 includes a specialized electrode or matrix of electrodes placed on the skin over the facial and trigeminal ganglia. The electrode geometry and pulse polarity can be controlled to achieve current steering or focusing to selectively target cell bodies in the ganglia while minimizing stimulation of surface cutaneous afferent nerves or surrounding muscles. Waveform pulse width, shape, or sequencing can be controlled to optimize selective activation of desired neurons (e.g. tactile afferent) while minimizing stimulation of undesired neurons (e.g. efferent motor or nociceptive).

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A method for non-invasively assisting neurorehabilitation in a patient for treatment of a disorder affecting sleep patterns, the method comprising:
   engaging a patient in an exercise, the patient having no cognitive, physical or emotional impairment with respect to the exercise;
   providing intraoral cutaneous stimulation of at least one of the patient's cranial nerves via a mouthpiece situated within the patient's mouth, the mouthpiece having an array of one or more electrodes disposed on at least one surface of the mouthpiece; and
   delivering electrical pulses from a pulse generator to the patient's tongue via the mouthpiece, the delivery of electrical pulses being contemporaneous with the patient's engagement in the exercise and independent of the patient's surrounding environment and the patient's engagement in the exercise.

2. The method of claim 1 wherein the electrodes have a circular cross section and have a diameter that is in a range of 1-10 mm.

3. The method of claim 2 wherein the electrodes are composed of at least one of gold, titanium, platinum, rhodium, stainless steel.

4. The method of claim 3 wherein the electrodes are insulating electrodes that include at least one of silicon oxide, titanium oxide, strontium oxide, or tin oxide.

5. The method of claim 4 further comprising delivering a capacitive displacement current through the mouthpiece, the capacitive displacement current flowing into the patient's tongue.

6. The method of claim 2 further comprising providing an electrically conductive material between the electrodes and the patient's tongue.

7. The method of claim 6 wherein the electrically conductive material is a conductive polymer.

8. The method of claim 1 further comprising delivering a first group of electrical pulses having a first frequency to a first group of electrodes on the mouthpiece and delivering a second group of electrical pulses having a second frequency to a second group of electrodes on the mouthpiece.

9. The method of claim 1 further comprising engaging the patient in one or more of the following: a brain training exercise, a computerized brain training exercise, a memory recollection exercise, an attention span increasing exercise, or a reading comprehension exercise.

10. The method of claim 1 further comprising engaging the patient in one or more of the following: a visualization exercise, a meditation exercise, or a relaxation exercise.

11. The method of claim 1 wherein the engaging step further comprises (i) having the patient perform the exercise at high intensity and (ii) subsequently having the patient perform the exercise at moderate intensity, while simultaneously providing the intraoral cutaneous stimulation to the patient's tongue.

12. The method of claim 1 wherein the engaging step further comprises having the patient perform the exercise at low intensity before performing the exercise at high intensity.

13. The method of claim 1 further comprising providing the intraoral cutaneous stimulation during one or more of a period shortly or immediately after the patient has engaged in the exercise or a period shortly or immediately prior to having the patient engage in the exercise, without taking measurements of electrical activity of the patient's brain during the one or more periods.

14. The method of claim 1 further comprising delivering the electrical pulses at an intensity level beneath the patient's threshold of sensory perception.

15. The method of claim 1 further comprising delivering electrical pulses to the patient's tongue in a random or repeating pattern that is independent of events occurring outside of the pulse generator and the mouthpiece.

16. The method of claim 1 further comprising engaging the patient in a cognitive exercise that includes delivery of queries to the patient via a computer, and requires the patient to supply responses to the computer.

17. The method of claim 1 further comprising engaging the patient in an exercise wherein the patient's ability to perform the exercise is hindered by insomnia.

18. The method of claim 1 wherein the electrical pulses delivered to the patient's tongue have a fundamental frequency of about 80 Hz.

19. The method of claim 1 wherein the electrical pulses delivered to the patient's tongue have a fundamental frequency in a range of 0.5-2.0 Hz.

20. The method of claim 1 wherein the electrical pulses delivered to the patient's tongue have a fundamental frequency in a range of 10-400 Hz.

21. The method of claim 1 wherein the electrical pulses delivered to the patient's tongue have a voltage in a range of 1-40 volts and deliver a current to the patient's tongue of about 0.5-50 mA.

22. The method of claim 1 wherein the electrical pulses delivered to the patient's tongue are between 1 and 500 microseconds in duration and have a frequency in a range of 1-1000 Hz.

23. The method of claim 1 wherein the electrical pulses delivered to the patient's tongue are delivered in groups, with each group having between 1 and 100 pulses and the groups being delivered at a rate in a range of 1-100 Hz.

24. The method of claim 1 wherein the electrical pulses delivered to the patient's tongue are between 25 and 50 microseconds in duration and have a frequency of about 80 Hz.

25. The method of claim 1 wherein the functional deficit comprises one or more of a muscular tremor, and an impairment of the patient's ability to make purposeful and planned movements of a limb.

26. The method of claim 1 where the functional deficit comprises one or more of an attention deficit, a memory impairment, and an impairment to the patient's ability to multitask.

27. The method of claim 1 wherein the disorder is insomnia.

28. A method for non-invasively assisting neurorehabilitation in a patient for treatment of a disorder affecting sleep patterns, the method comprising:
(a) engaging a patient in an exercise, the patient having no cognitive, physical or emotional impairment with respect to the exercise;
(b) providing intraoral cutaneous stimulation of at least one of the patient's cranial nerves via an array of electrodes placed on the patient's skin at the patient's face; and
(c) delivering electrical pulses from a pulse generator to the patient's skin via the array of electrodes, the delivery of electrical pulses being contemporaneous with the patient's engagement in the exercise and independent of the patient's surrounding environment and the patient's engagement in the exercise.

29. The method of claim 28 wherein the electrodes have a circular cross section and have a diameter that is in a range of 1-10 mm.

30. The method of claim 29 wherein the electrodes are composed of at least one of gold, titanium, platinum, rhodium, stainless steel.

31. The method of claim 30 wherein the electrodes are insulating electrodes that include at least one of silicon oxide, titanium oxide, strontium oxide, or tin oxide.

32. The method of claim 31 further comprising delivering a capacitive displacement current through the mouthpiece, the capacitive displacement current flowing into the patient's intraoral cavity.

33. The method of claim 29 further comprising providing an electrically conductive material between the electrodes and the patient's intraoral cavity.

34. The method of claim 33 wherein the electrically conductive material is a conductive polymer.

35. The method of claim 28 further comprising delivering a first group of electrical pulses having a first frequency to a first group of electrodes on the mouthpiece and delivering a second group of electrical pulses having a second frequency to a second group of electrodes on the mouthpiece.

36. The method of claim 28 wherein engaging a patient in an exercise further comprises engaging the patient in one or more of a brain training exercise, a computerized brain training exercise, a memory recollection exercise, an attention span increasing exercise, or a reading comprehension exercise.

37. The method of claim 28 wherein engaging a patient in an exercise further comprises engaging the patient in one or more of the following: a visualization exercise, a meditation exercise, or a relaxation exercise.

38. The method of claim 28 wherein the engaging step further comprises (i) having the patient perform the exercise at high intensity and (ii) subsequently having the patient perform the exercise at moderate intensity, while simultaneously providing the intraoral cutaneous stimulation to the patient's skin at the patient's face.

39. The method of claim 28 wherein the engaging step further comprises having the patient perform the exercise at low intensity before performing the exercise at high intensity.

40. The method of claim 28 further comprising providing the intraoral cutaneous stimulation during one or more of a period shortly or immediately after the patient has engaged in the exercise or a period shortly or immediately prior to having the patient engage in the exercise, without taking measurements of electrical activity of the patient's brain during the one or more periods.

41. The method of claim 28 further comprising delivering the electrical pulses at an intensity level beneath the patient's threshold of sensory perception.

42. The method of claim 28 further comprising delivering electrical pulses to the patient's skin at the patient's face in a random or repeating pattern that is independent of events occurring outside of the pulse generator and the mouthpiece.

43. The method of claim 28 further comprising engaging the patient in a cognitive exercise that includes delivery of queries to the patient via a computer, and requires the patient to supply responses to the computer.

44. The method of claim 28 further comprising engaging the patient in an exercise wherein the patient's ability to perform the exercise is hindered by insomnia.

45. The method of claim 28 wherein the electrical pulses delivered to the patient's intraoral cavity have a fundamental frequency of about 80 Hz.

46. The method of claim 28 wherein the electrical pulses delivered to the patient's intraoral cavity have a fundamental frequency in a range of 0.5-2.0 Hz.

47. The method of claim 28 wherein the electrical pulses delivered to the patient's tongue have a fundamental frequency in a range of 10-400 Hz.

48. The method of claim 28 wherein the electrical pulses delivered to the patient's intraoral cavity have a voltage in a range of 1-40 volts and deliver a current to the patient's intraoral cavity of about 0.5-50 mA.

49. The method of claim 28 wherein the electrical pulses delivered to the patient's intraoral cavity are between 1 and 500 microseconds in duration and have a frequency in a range of 1-1000 Hz.

50. The method of claim 28 wherein the electrical pulses delivered to the patient's intraoral cavity are delivered in groups, with each group having between 1 and 100 pulses and the groups being delivered at a rate in a range of 1-100 Hz.

51. The method of claim 28 wherein the electrical pulses delivered to the patient's intraoral cavity are between 25 and 50 microseconds in duration and have a frequency of about 80 Hz.

52. The method of claim 28 wherein the impairment comprises one or more of a muscular tremor, and an impairment of the patient's ability to make purposeful and planned movements of a limb.

53. The method of claim 28 where the impairment comprises one or more of an attention deficit, a memory impairment, and an impairment to the patient's ability to multitask.

54. The method of claim 28 further comprising:
(d) ceasing stimulation to the patient's skin for a period of time; and
(e) repeating the foregoing steps (a), (b), and (c), wherein the patient engages in one or more of:
(1) the exercise at a different level of intensity; and
(2) a second exercise different from the exercise.

55. The method of claim 28 wherein the disorder is insomnia.

* * * * *